United States Patent
Beak

(10) Patent No.: US 10,188,366 B2
(45) Date of Patent: Jan. 29, 2019

(54) X-RAY IRRADIATION CONTROLLING DEVICE

(71) Applicant: Rayence Co., Ltd., Gyeonggi-do (KR)

(72) Inventor: In Jae Beak, Gyeonggi-do (KR)

(73) Assignee: Rayence Co., Ltd., Gyeonggi-do (KR)

( * ) Notice: Subject to any disclaimer, the term of this patent is extended or adjusted under 35 U.S.C. 154(b) by 185 days.

(21) Appl. No.: 15/125,592

(22) PCT Filed: Mar. 13, 2015

(86) PCT No.: PCT/KR2015/002437
§ 371 (c)(1),
(2) Date: Sep. 13, 2016

(87) PCT Pub. No.: WO2015/137759
PCT Pub. Date: Sep. 17, 2015

(65) Prior Publication Data
US 2017/0000445 A1    Jan. 5, 2017

(30) Foreign Application Priority Data
Mar. 14, 2014    (KR) ........................ 10-2014-0030072

(51) Int. Cl.
*H05G 1/10*    (2006.01)
*A61B 6/04*    (2006.01)
(Continued)

(52) U.S. Cl.
CPC ................ *A61B 6/542* (2013.01); *A61B 6/10* (2013.01); *A61B 6/4233* (2013.01); *A61B 6/488* (2013.01);
(Continued)

(58) Field of Classification Search
CPC ....... A61B 6/4233; A61B 6/527; A61B 6/542; A61B 6/545; A61B 6/548; A61B 6/585;
(Continued)

(56) References Cited

U.S. PATENT DOCUMENTS

2010/0246759 A1    9/2010    Ogura et al.
2012/0163533 A1    6/2012    Ogura et al.
(Continued)

FOREIGN PATENT DOCUMENTS

JP    2008-167928 A    7/2008
JP    2013-138828 A    7/2013
(Continued)

*Primary Examiner* — Irakli Kiknadze
(74) *Attorney, Agent, or Firm* — IP Legal Services, LLC

(57) ABSTRACT

The present invention provides a digital X-ray image system, an X-ray irradiation controlling device, and a method therefor in order to find out a main-shot condition for obtaining a main-shot radiograph signal on the basis of a radiograph signal (for example, a reference pixel value) outputted in response to a pre-shot condition using specific characteristics between a radiograph signal (pixel value) and a radiograph condition. The X-ray irradiation controlling device includes: a pre-shot radiography condition determiner determining a radiography condition; a reference pixel value acquirer acquiring a reference pixel value from a pre-shot radiograph obtained under the pre-shot radiography condition; an interrelation acquirer acquiring interrelation between a radiography condition and a radiograph signal on the basis of the reference pixel value; and a main-shot radiography condition determiner determining a main-shot radiography condition using the interrelation.

5 Claims, 6 Drawing Sheets

(51) Int. Cl.
*A61B 6/00* (2006.01)
*A61B 6/10* (2006.01)

(52) U.S. Cl.
CPC .............. *A61B 6/502* (2013.01); *A61B 6/544* (2013.01); *A61B 6/545* (2013.01); *A61B 6/585* (2013.01); *A61B 6/0414* (2013.01)

(58) Field of Classification Search
CPC ......... A61B 6/0414; A61B 6/10; A61B 6/488; A61B 6/502; A61B 6/544; A61B 6/583; A61B 6/5217; A61B 5/015; A61B 6/481; A61B 6/5205; A61B 2017/00084; A61B 2018/2005; A61B 5/055; A61B 6/4291; A61B 6/4441; A61B 6/463; A61B 6/469; A61B 6/54; A61B 6/504; A61B 6/4035; A61B 6/482; A61B 6/42; H04N 5/235; H04N 5/32; G01N 23/04

USPC ...................................... 378/19, 62, 95, 98.8
See application file for complete search history.

(56) References Cited

U.S. PATENT DOCUMENTS

| 2013/0148782 | A1 | 6/2013 | Tajima |
| 2014/0064444 | A1* | 3/2014 | Oh .................. A61B 6/482 378/37 |
| 2014/0185762 | A1* | 7/2014 | Lee .................. G01N 23/04 378/62 |
| 2014/0219422 | A1 | 8/2014 | Nishino et al. |

FOREIGN PATENT DOCUMENTS

| KR | 10-2010-0109381 A | 10/2010 |
| KR | 10-2013-0014723 A | 2/2013 |
| WO | 2013/065515 A1 | 5/2013 |

\* cited by examiner

X-RAY IRRADIATION CONTROLLING DEVICE

CROSS REFERENCE TO RELATED APPLICATIONS

This application is a National Stage Patent Application of PCT International Patent Application No. PCT/KR2015/002437 (filed on Mar. 13, 2015) under 35 U.S.C. § 371, which claims priority to Korean Patent Application No. 10-2014-0030072 (filed on Mar. 14, 2014), the teachings of which are incorporated herein in their entireties by reference.

TECHNICAL FIELD

The present invention relates to a digital X-ray image system and, more particularly, to a digital X-ray image system, an X-ray irradiation controlling device, and a method therefor.

BACKGROUND ART

Artificial radiation sources have been recognized to radiate a large amount of radioactive rays in comparison to natural radiation sources. For example, the exposure dose by one-time X-ray scanning corresponds to the exposure dose by natural radiation for one year in some cases.

Despite this circumstance, medical use of radiation is socially accepted because in many cases the use of radiation is inevitable in order to treat patients. Radiation treatment should be justified on the basis of EBM (Evidence Based Medicine) and should obey limitations for as low exposure dose as possible within a range of obtaining useful medical information together with optimization against radiation.

Existing film type of diagnostic X-ray systems measure an X-ray dose using an ion chamber installed at the front end of a film to measure an X-ray dose.

However, such an ion chamber has a complicated structure due to a plurality of electrodes and is difficult to reduce in size, so there is a need for installing expensive equipment ahead of a detector.

Recently, not the film type, but a CCD type or flat panel type X-ray detector (hereafter, referred to as an "FPD") has been used. The FPD has a sensing membrane on a substrate, and detects radiation reaching the sensing membrane, converts the detected radiation into charge, and accumulates the charge in a capacitor having two-dimensional array. The accumulated charge is sensed when a switching device is turned on and transmitted as a radiation detection signal to a image processor. The image processor obtains a radiograph having pixels based on the radiation detection signal.

Using the FPD makes it easy and simple to keep and process a radiograph without complicated distortion in detection, as compared with the film type used in the related art. Therefore, the FPD is advantageous in terms of the structure of the system and image processing.

However, when an image system including the FPD is used to radiograph an object, the larger the tube voltage (kVp) and the radiation dose (mAs), the larger the exposure dose to the object.

In contrast, when the tube voltage (kVp) or the radiation dose (mAs) is reduced, the luminance of a radiograph obtained by the FPD is reduced, so it is difficult to interpret the radiograph.

Therefore, there is a need for X-ray radiograph that minimizes the exposure dose to an object and provides an appropriate luminance for a radiograph obtained by the FPD.

According to the film type in the related art, an ion chamber needs to be disposed ahead of a detector to measure an X-ray dose and it is required to adjust the conditions for X-ray radiography in accordance with the amount of X-ray radiated to the ion chamber. On the other hand, according to a CCD type or a flat panel type in which an ion chamber actually cannot be installed, radiography is performed on the basis of radiograph conditions including the tube voltage (kVp) or the radiation dose (mAs) of an X-ray type, and for this purpose, a lookup table (LUT) about each part to be radiographed of an object so that an operator determines radiography conditions in consideration of the sex, age, and weight on the basis of the lookup table.

Accordingly, the CCD type or the flat panel type of the related art do not use the way of obtaining an optimal radiograph with the minimum exposure dose by precisely determining the tube voltage and the radiation dose (mAs) in accordance with the physical features of an object, but depends on only on an operator's skill based on experience in radiographing an object.

There has been proposed a "Radiation imaging apparatus" for radiographing an object in Korean Patent Application No. 10-2010-0022618. The apparatus includes: an electromagnetic ray generator that radiates a plurality of electromagnetic rays to an object using a plurality of electronic sources arranged in a one-dimensional or two-dimensional array; an electromagnetic ray detector that obtains a plurality of first radiographs by detecting electromagnetic rays that are radiated through an object at different angles when the apparatus is in operation; an area specifier that specifies an area on an object using the first radiographs obtained by the electromagnetic ray detector; and a determiner that determines an electronic source to be operated of the electronic sources on the basis of the area on the object specified by the area specifier, in which a second radiograph is obtained by the electromagnetic ray generated by the electronic source determined by the determiner. According to this mammography system that is used for radiographing breasts, the luminance of an area on an object is determined on the basis of a first radiograph obtained through a pre-shot process, which radiates an X-ray in advance, and then a corresponding main-shot is actually radiated in order to obtain an appropriate radiograph having a desired luminance of breast tissues because objects have different breast tissues and sizes.

DISCLOSURE

Technical Problem

Accordingly, according to the related art, an accurate main-shot condition cannot be found through a pre-shot and lookup table (LUT) values are simply estimated by a pre-shot, so that it is impossible to quickly obtain an appropriate radiograph and an object of the present invention is to solve this problem.

An object of the present invention is to provide a digital X-ray image system, an X-ray irradiation controlling device, and a method thereof in order to find out a main-shot condition for obtaining a main-shot radiograph signal on the basis of a radiograph signal (for example, a reference pixel value) outputted in response to a pre-shot condition using specific characteristics between a radiograph signal (pixel value) and a radiograph condition.

The objects of the invention are not limited to the objects described above, and other objects and advantages of the present invention stated herein may be easily understood from the following description and may be made clear by embodiments of the present invention. Further, it will be easily understood that the objects and advantages of the present invention can be accomplished by the configurations and combinations of them described in claims.

Technical Solution

In order to achieve the above object, according to one aspect of the present invention, there is provided an X-ray irradiation controlling device including: a pre-shot radiography condition determiner determining a radiography condition; a reference pixel value acquirer acquiring a reference pixel value from a pre-shot radiograph obtained under the pre-shot radiography condition; an interrelation acquirer acquiring interrelation between a radiography condition and a radiograph signal on the basis of the reference pixel value; and a main-shot radiography condition determiner determining a main-shot radiography condition using the interrelation.

According to another aspect of the present invention, there is provided an X-ray irradiation controlling method including: determining a radiography condition; acquiring a reference pixel value from a pre-shot radiograph obtained under the pre-shot radiography condition; acquiring interrelation between a radiography condition and a radiograph signal on the basis of the reference pixel value; and determining a main-shot radiography condition using the interrelation.

According to another aspect of the present invention, there is provided a digital X-ray image system that performs main-shot radiography after pre-shot radiography, in which a luminance difference at highest-density areas of main-shot radiographs of an object under a main-shot radiography condition is within a critical value.

Advantageous Effects

According to the present invention, it is possible to find out a main-shot condition for obtaining a main-shot radiograph signal on the basis of a radiograph signal (for example, a reference pixel value) outputted in response to a pre-shot condition using specific characteristics between a radiograph signal (pixel value) and a radiograph condition.

Further, it is possible to find out an accurate main-shot radiography condition through pre-shot radiography, so it is possible to quickly obtain an appropriate radiograph.

MODE FOR INVENTION

The objects, features, and advantages of the present invention will be made clear from the following detailed description, and accordingly, those skilled in the art could easily implement the spirit of the present invention. Further, in describing the present invention, well-known functions or constructions will not be described in detail since they may unnecessarily obscure the understanding of the present invention. Hereinafter, exemplary embodiments of the present invention will be described with reference to accompanying drawings.

Throughout this specification, a case in which any one part is connected with the other part includes a case in which the parts are directly connected with each other and a case in which the parts are indirectly connected with each other with other elements interposed therebetween. Further, unless explicitly described otherwise, "comprising" any components will be understood to imply the inclusion of other components rather than the exclusion of any other components. Further, even if some components are expressed by singular forms throughout the specification, the present invention is not limited thereto and the components may be plural parts.

Figure 1:
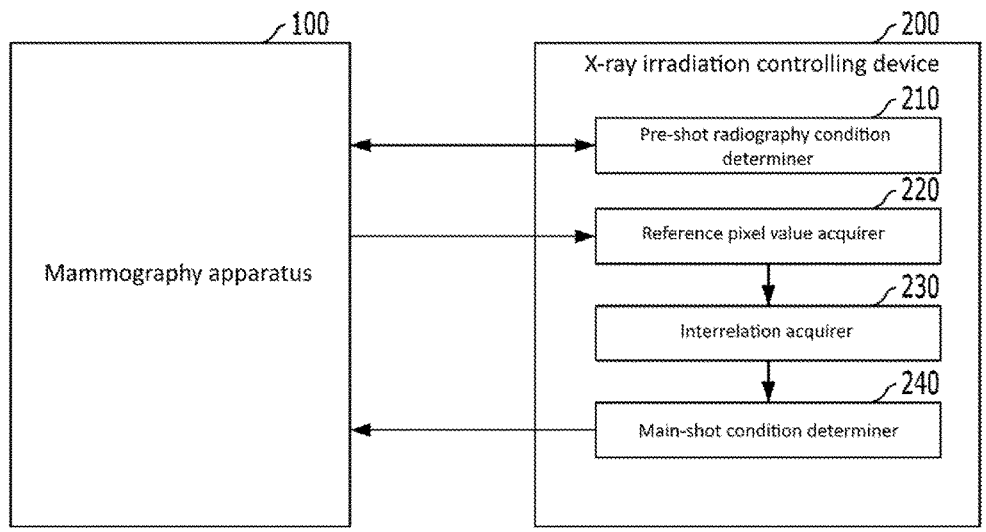
FIG. 1 is a diagram showing the configuration of an X-ray irradiation controlling device in a digital X-ray image system according to an embodiment of the present invention.

FIG. 1 is a diagram showing the configuration of an X-ray irradiation controlling device in a digital X-ray image system according to an embodiment of the present invention.

In a digital X-ray image system using a digital X-ray detector, generally, it is impossible to adjust a radiation dose using a dosimeter (a device for controlling a radiation dose). In order to solve this problem, an embodiment of the present invention proposes a method of adjusting X-ray radiography conditions (an apparatus and method for controlling X-ray radiation) based on radiograph signals from a digital X-ray detector.

As shown in FIG. 1, a digital X-ray image system according to an embodiment of the present invention includes a mammography apparatus 100 and an X-ray irradiation controlling device 200.

The mammography apparatus 100, which is a breast radiography apparatus, includes an X-ray tube, a compress, and a digital X-ray detector, etc., and is well known and used in the art, so the detailed description is not provided herein.

The X-ray irradiation controlling device 200 includes a pre-shot radiography condition determiner 210 for determining pre-shot radiography conditions, a reference pixel value acquirer 220 for acquiring a reference pixel value from a pre-shot radiograph obtained under a determined pre-shot radiography condition, an interrelation acquirer 230 for obtaining the interrelation between a radiography condition, particularly a radiation dose (mAs) and a radiograph on the basis of the acquired reference pixel value, and a main-shot condition determiner 240 for determining a main-shot radiography condition using the acquired interrelation.

Next, the pre-shot radiography condition determiner 210, reference pixel value acquirer 220, interrelation acquirer 230, and main-shot radiography condition determiner 240 are described in detail hereafter.

First, the pre-shot radiography condition determiner 210 determines pre-shot conditions such as a pre-shot tube voltage and a pre-shot radiation dose depending on a breast thickness, and the mammography apparatus 100 performs pre-shot radiography at the pre-shot tube voltage and the pre-shot radiation dose according to the pre-shot radiography condition before main-shot radiography and transmits a pre-shot radiograph to the reference pixel value acquirer 220.

Equations for finding out the pre-shot voltage (kVp) according to a breast thickness by an embodiment of the present invention are described hereafter.

First, a basic equation is the following Equation 1. For reference, Equation 1 is applied to set efficient ranges of the pre-shot voltage (kVp) that is determined by the pre-shot radiography condition determiner 210 and the main-shot radiation dose that is determined by the main-shot radiography condition determiner 240, and is also applied to determine a target pixel value (TPV) that a reference value is supposed to reach.

$$Y = (\text{y\_max} - \text{y\_min}) \times \left(\frac{x - \text{x\_min}}{\text{x\_max} - \text{x\_min}}\right)^y + \text{y\_min} \quad \text{[Equation 1]}$$

where y axis may be any one of the tube voltage (kVp), the target pixel value (TPV), and the radiation dose. Accordingly, y_min is the lower limit (y axis) of Y (any one of kVP, TPV, and mAs) and y_max is the upper limit (y axis) of Y (any one of kVP, TPV, and mAs).

Further, x axis may be a breast thickness. Mammography is started with an object to the radiographed pressed, so it receives feedback of pressed thickness information after pressing. Accordingly, x is the thickness of the object to be radiographed, that is, the breast thickness. Further, x_min is the lower limit of an x-axial variation section, that is, the lower limit (x axis) of the breast thickness and x_max is the upper limit of the x-axial variation section, that is, the upper limit (x axis) of the breast thickness.

Further, γ is a rate of change (an increase rate) of the variation section.

On the other hand, an equation for finding out a pre-shot tube voltage (kVp) according to a breast thickness is the following Equation 2.

$$kVp = (\text{kVp\_max} - \text{kVp\_min}) \times \left(\frac{\text{thick} - \text{thick\_min}}{\text{thick\_max} - \text{thick\_min}}\right)^y + \text{kVp\_min} \quad \text{[Equation 2]}$$

where kVp_min is the lower limit of a variation section of the tube voltage (kVp) and kVp_max is the upper limit of a variation section of the tube voltage (kVp). Further, Thick is the thickness of the object to be radiographed now, that is, the breast thickness. Thick_min is the lower limit of the breast thickness and Thick_max is the upper limit of the breast thickness. kVp_min, kVp_max, Thick_min, Thick_max, γ are values determined in advance in accordance with the purpose of radiography or the characteristics of the mammography apparatus 100, so it is possible to determine the pre-shot tube voltage (kVp) according to the breast thickness when knowing only the breast thickness.

Accordingly, the pre-shot radiography condition determiner 210 can determine the pre-shot tube voltage according to a breast thickness using Equation 2. The relationship between a breast thickness and a tube voltage (kVp) by Equation 2 is indicated by kVp in the graph of FIG. 10.

Further, the pre-shot radiation amount, which is a predetermined radiation dose, may be the minimum radiation dose for obtaining radiograph, for example, 5 mAs.

Next, the reference pixel value acquirer 220 acquires a reference pixel value by searching an area having the lowest signal in a pre-shot radiograph. The area having the lowest signal in a pre-shot radiograph is the part that has high density and transmits the smallest amount of X-rays in an object, and the contrast of this part should be a predetermined level or higher in order to easily obtain and read out a high-quality radiograph.

Accordingly, the interrelation acquirer 230 acquires the interrelation between a radiography condition, particularly, a radiation dose (mAs) and a radiograph signal on the basis of the reference pixel value and the pre-shot radiography conditions etc. Radiograph signals acquired from the digital X-ray detector have a linear characteristic to the radiation dose. Accordingly, it is possible to obtain the interrelation between a pre-shot radiograph image obtained at a pre-shot radiation dose under the pre-shot radiography conditions before main-shot radiography, a radiation dose (mAs) and a radiograph signal based on a pre-shot radiation dose, which can be expressed in a numerical formula (for example, y=ax+b).

Accordingly, the main-shot radiography condition determiner 240 determines the interrelation between the radiation dose (mAs) and the radiograph signal, that is, determines the main-shot radiography conditions, particularly, the main-shot radiation dose using the numerical formula. In other words, it may be possible to determine the main-shot radiography conditions by calculating the main-shot radiation dose (mAs) for adjusting the reference pixel value to a desired target pixel value using the interrelation (for example, numerical formula). Further, the pre-shot tube voltage determined before by the pre-shot radiography condition determiner 210 is equally used for the main-shot tube voltage.

The mammography apparatus 100 outputs a main-shot radiograph by performing main-shot radiography in accordance with the calculated radiography conditions.

Figure 2:
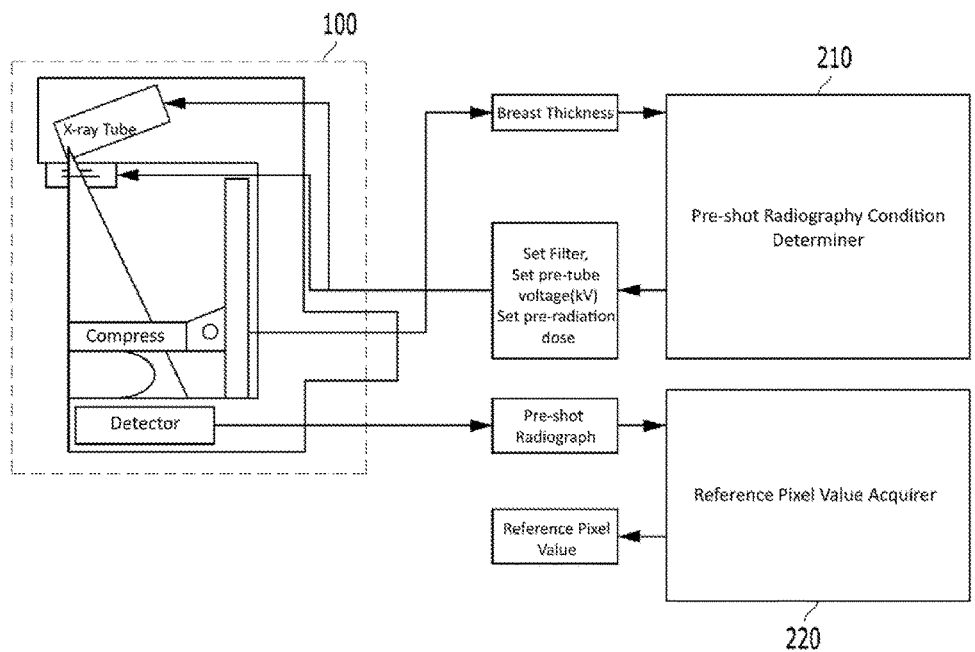
FIG. 2 is a diagram for illustrating in detail a pre-shot condition determiner and a reference pixel value acquirer according to an embodiment of the present invention.

FIG. 2 is a diagram for illustrating in detail the pre-shot radiography condition determiner 210 and the reference pixel value acquirer 220 according to an embodiment of the present invention. For example, FIG. 2 shows a method of determining a pre-shot radiography condition in response to a breast thickness measured by the mammography apparatus 100 and then obtaining a reference pixel value from a pre-shot radiograph obtained under the determined pre-shot condition.

Figure 10:
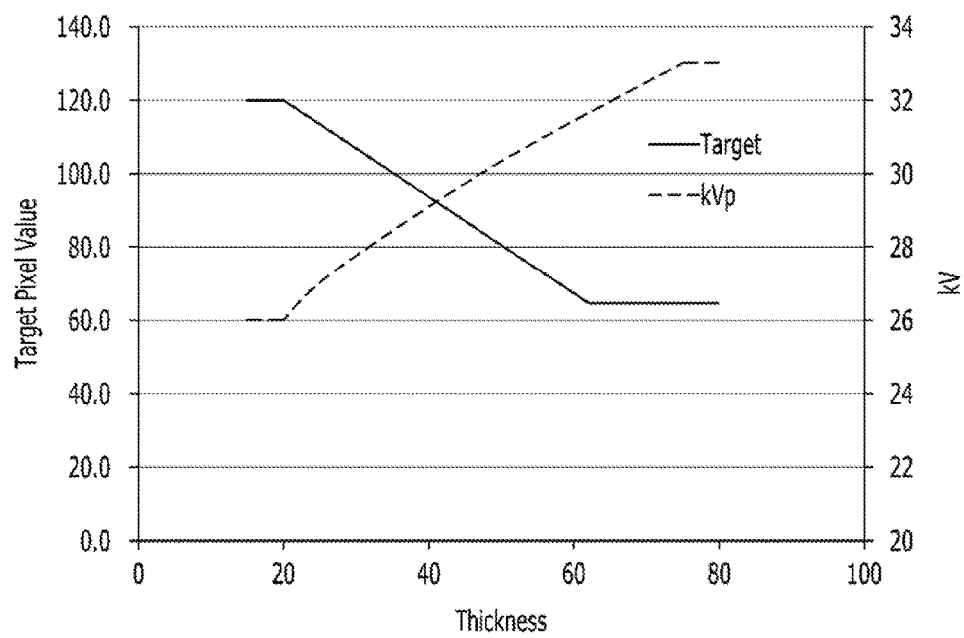
FIG. 10 is a diagram showing a tube voltage and a target pixel value (TPV) depending on the thickness of a breast according to an embodiment of the present invention.

As shown in FIG. 2, when receiving a breast thickness (that is, the thickness of an object) pressed by the compress of the mammography apparatus 100, the pre-shot radiography condition determiner 210 find outs a pre-shot voltage (kV, for example a value in the range of 26 kV to 33 kV) according to the breast thickness (for example, which may be a value in the range of 1.5 cm to 8 cm) inputted from Equation 2 or the graph indicated by kVp in FIG. 10.

The pre-shot radiography condition determiner 210 determines a filter before or after determining the pre-shot voltage kV, which is described in detail hereafter.

Figure 3:
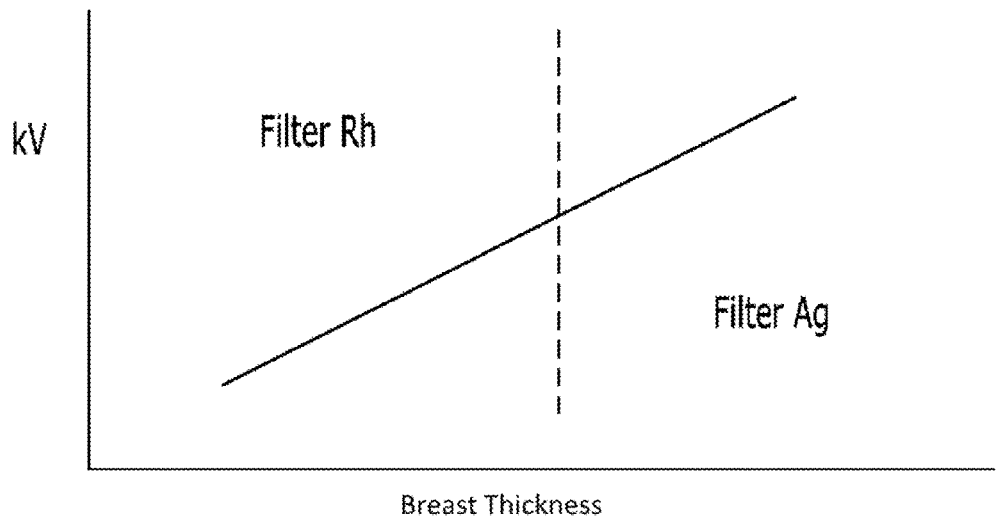
FIG. 3 is a diagram for illustrating a way of finding out a pre-shot tube voltage corresponding to the thickness of a breast according to an embodiment of the present invention.

The tube voltage (kV) determines the quality of an X-ray, which means transmission ability for X-rays. For example, when a breast is thick and has high density, high transmission ability is required, so the tube voltage should be increased. However, there is a method of improving the transmission ability for X-rays by increasing the average photon energy of X-rays using a filter without increasing a tube voltage, and the method generally uses a rhodium (Rh) filter and a silver (Ag) filter when a mammography system uses a tungsten (W) target. In this case, the rhodium (Rh) filter is used for a thin breast and the silver (Ag) filter is used for a thick breast. Accordingly, the pre-shot radiography condition determiner 210 can correct a pre-shot tube voltage (kVp), depending on the current used filter before or after determining the pre-shot tube voltage (kVp). For reference, the relationship between a breast thickness and a tube voltage when a rhodium (Rh) filter or a silver (Ag) filter is used is shown in FIG. 3.

As described above, the pre-shot radiography condition determiner 210 determines a pre-shot radiography condition by performing the process of determining a filter, the process of determining a pre-shot determiner according to a breast thickness, and the process of determining a pre-shot radiation dose. The pre-shot radiation dose, which is a predetermined radiation dose, may be the minimum radiation dose for obtaining a radiograph, for example, 5 mAs, or may be any value in the range of 5-10 mAs.

Then, the mammography apparatus 100 receives the determined pre-shot radiography condition, performs pre-shot radiography at the pre-shot voltage according to the breast thickness and the pre-shot radiation dose determined in accordance with the inputted pre-shot radiography condition, and transmits the obtained pre-shot radiograph to the reference pixel value acquirer 220.

Figure 4:
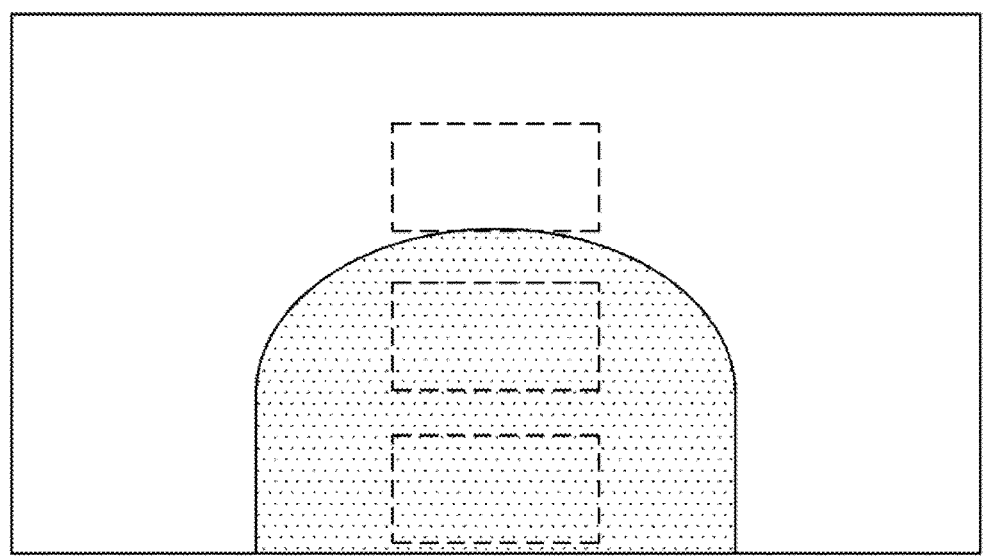
FIGS. 4 and 5 are diagrams for illustrating a way of acquiring a reference pixel value according to an embodiment of the present invention.
Figure 5:
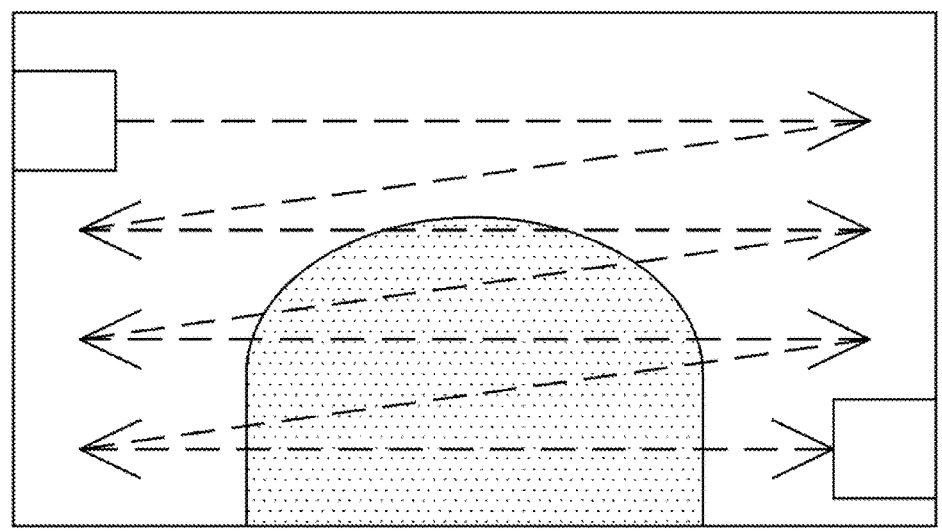

Then, the reference pixel value acquirer 220 acquires a reference pixel value by searching the area having the lowest signal (that is, the part having high density to transmit a smallest amount of X-rays) in the received pre-shot radiograph. The reference pixel value acquirer 220, as shown in FIG. 4, selects at least one position ROI1, ROI2, or ROI3 in the pre-shot radiograph and compares the luminance, or as shown in FIG. 5, finds out a position where the radiograph signal is the lowest by sequentially moving (scanning) the pre-shot radiograph and acquires the pixel value at the position as the reference pixel value.

Figure 6:
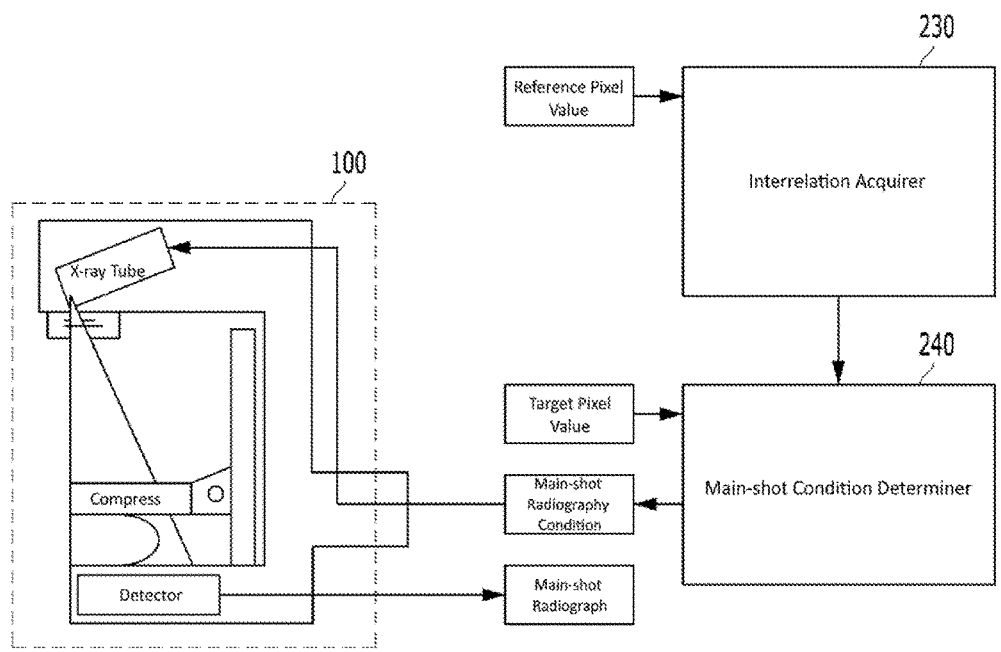
FIG. 6 is a diagram for illustrating in detail an interrelation acquirer and a main-shot condition determiner according to an embodiment of the present invention.

FIG. 6 is a diagram for illustrating in detail the interrelation acquirer 230 and the main-shot radiography determiner 240 according to an embodiment of the present invention, which shows a method of acquiring the interrelation (linear relation) between a radiation dose and a radiograph signal on the basis of a reference pixel value and of determining a main-shot radiography condition using the acquired interrelation.

Figure 7:
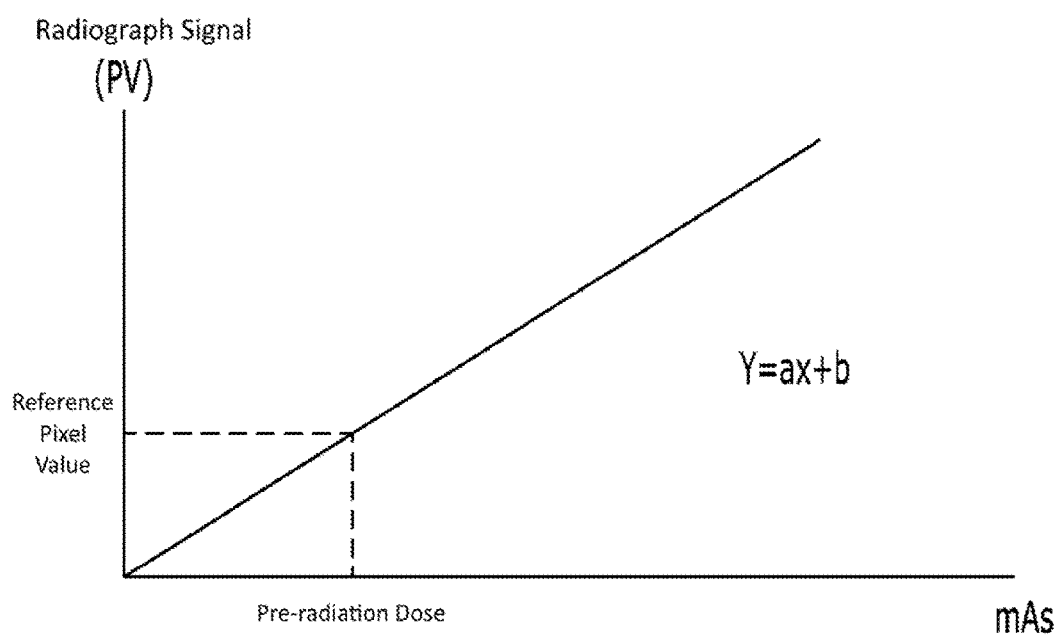
FIG. 7 is a diagram showing the interrelation between a radiation dose and a corresponding reference pixel value in pre-shot radiography according to an embodiment of the present invention.

As shown in FIG. 6, the interrelation acquirer 230 can acquire the interrelation between a radiation dose (mAs) and a radiograph signal on the basis of a predetermined pre-shot radiography condition and a reference pixel value acquired by the reference pixel value acquirer 220, which an be expressed in a numerical formula (for example, y=ax+b). That is, as shown in FIG. 7, the interrelation acquirer 230 can acquire the interrelation (a linear relation) between a pre-shot radiation dose in pre-shot radiography and a corresponding reference pixel value and express the relationship in a numerical formula, for example, y=ax+b. In this case, x is the pre-shot radiation dose in pre-shot radiography, y is a reference pixel value acquired in accordance with the radiation dose in the pre-shot radiography, and a and b are constants.

Figure 8:
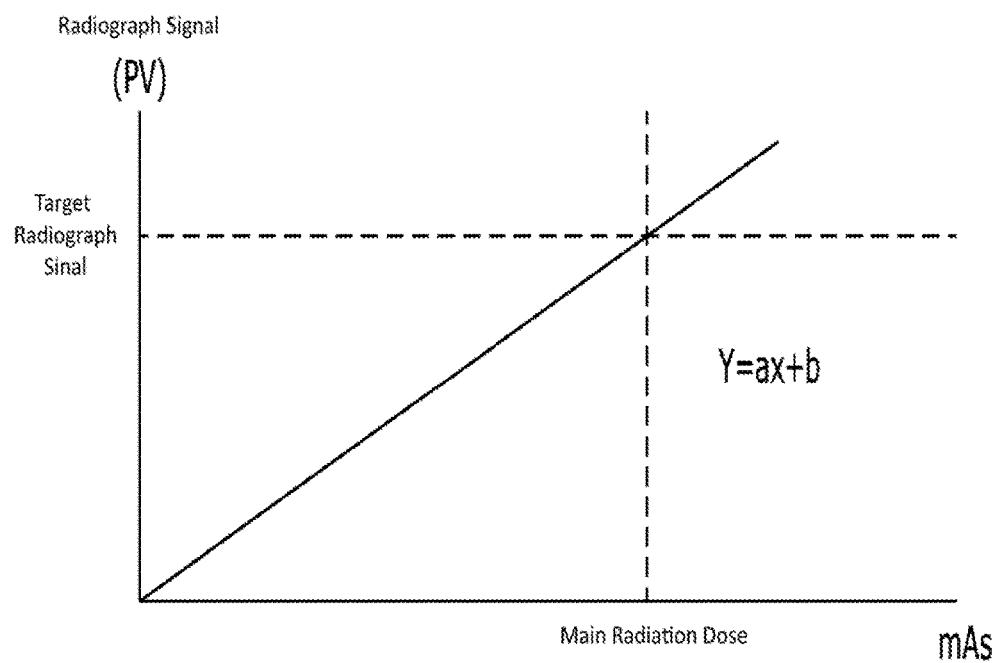
FIG. 8 is a diagram for illustrating a method of calculating a main-shot dose for obtaining a target radiograph image using an interrelation according to an embodiment of the present invention.
Figure 9:
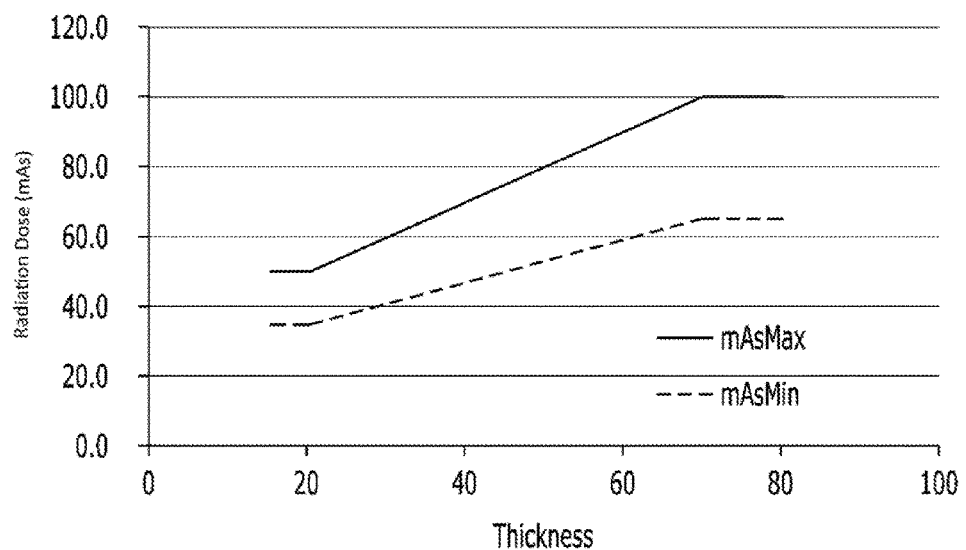
FIG. 9 is a diagram showing a radiation dose range according to the thickness of a breast according to an embodiment of the present invention.

As shown in FIG. 6, the main-shot radiography condition determiner 240 calculates a main-shot radiography condition using the interrelation. In other words, as shown in FIGS. 7 and 8, the main-shot radiography condition determiner 240 can calculate a main-shot radiation dose (mAs) for adjusting a radiograph signal at a reference pixel value to a radiograph signal of a desired target pixel value. The calculated main-shot radiation dose (mAs), as shown in FIG. 9, may be a value (in a radiation dose range) between the maximum (mAsMax) of a radiation dose that can be inputted in accordance with a breast thickness and the minimum (mAsMin) of a radiation dose that can be inputted in accordance with the breast thickness. If the calculated main-shot radiation dose is out of the radiation dose range, it is possible to determine the final main-shot radiation dose by correcting the calculated main-shot radiation dose within the radiation dose range. Further, a pre-shot tube voltage determined in advance in accordance with a breast thickness may be used for the main tube voltage of the main-shot radiography conditions.

In FIG. 9, the graph indicated by mAsMax is obtained by substituting the maximum and the minimum within the maximum critical band of a radiation dose that can be inputted for each breast thickness into Equation 1, while the graph indicated by mAsmin is obtained by substituting the maximum and the minimum within the minimum critical band of a radiation dose that can be inputted for each breast thickness into y_max and y_min in Equation 1, in which the breast thickness and the radiation dose are x axis and y axis, respectively. Accordingly, the main-shot radiation dose for each breast thickness calculated by the main-shot radiography condition determiner 240 is supposed to be between mAsMax and mAsMin for the same breast thickness, but when the main-shot radiation dose is not in this range, mAsMax and mAsMin for a corresponding breast thickness is determined as the final main-shot radiation dose.

In this case, the target pixel value is determined in accordance with the breast thickness and the following Equation 3 is the equation for finding out a target pixel value at a breast thickness.

$$TPV = (TPV\_max - TPV\_min) \times \left(\frac{thick - thick\_min}{thick\_max - thick\_min}\right)^y + TPV\_min \quad \text{[Equation 3]}$$

where TPV_min is the lower limit of a variation section of a target pixel value (TPV) and TPV_max is the upper limit of the variation section of the target pixel value (TPV). Further, the relationship between a breast thickness and a target pixel value (TPV) obtained from the above relationship is indicated by Target in FIG. 10. The graph indicated by Target in FIG. 10 shows a target pixel value (TVP) for each breast thickness determined by Equation 3, so it is possible to find out a desired target pixel value for an actual breast thickness from the graph. Further, it is possible to find out a main-shot radiation dose by substituting the target pixel value for a breast thickness into the linear relationship shown in FIG. 7 or 8.

Next, the mammography apparatus 100 outputs a main-shot radiograph by performing main-shot radiography in accordance with a main-shot radiography condition such as the calculated main-shot radiation dose (mAs). The main-shot tube voltage may be a pre-shot tube voltage according to a breast thickness determined before by the pre-shot radiography condition determiner 210.

As a result, by using the X-ray irradiation controlling device and method in the digital X-ray image system according to the present invention, 'the difference of luminance at a highest-density area (for example, an interesting area)' in the 'main-shot radiographs of an object obtained in accordance with main-shot radiography conditions' shows a value within a critical value (for example, within 10%), which is an important characteristic of the present invention.

As described above, a radiograph signal (pixel value) obtained from a digital X-ray detector has a linearity to a radiation dose (mAs). Accordingly, by using this characteristic, it is possible to find out a main-shot radiation dose for main-shot radiography for obtaining a desired radiograph signal, that is, a target radiograph signal on the basis of a radiograph signal (for example, a reference pixel value) outputted in response to a pre-shot radiation dose transmitted to the digital X-ray detector.

Figure 11:
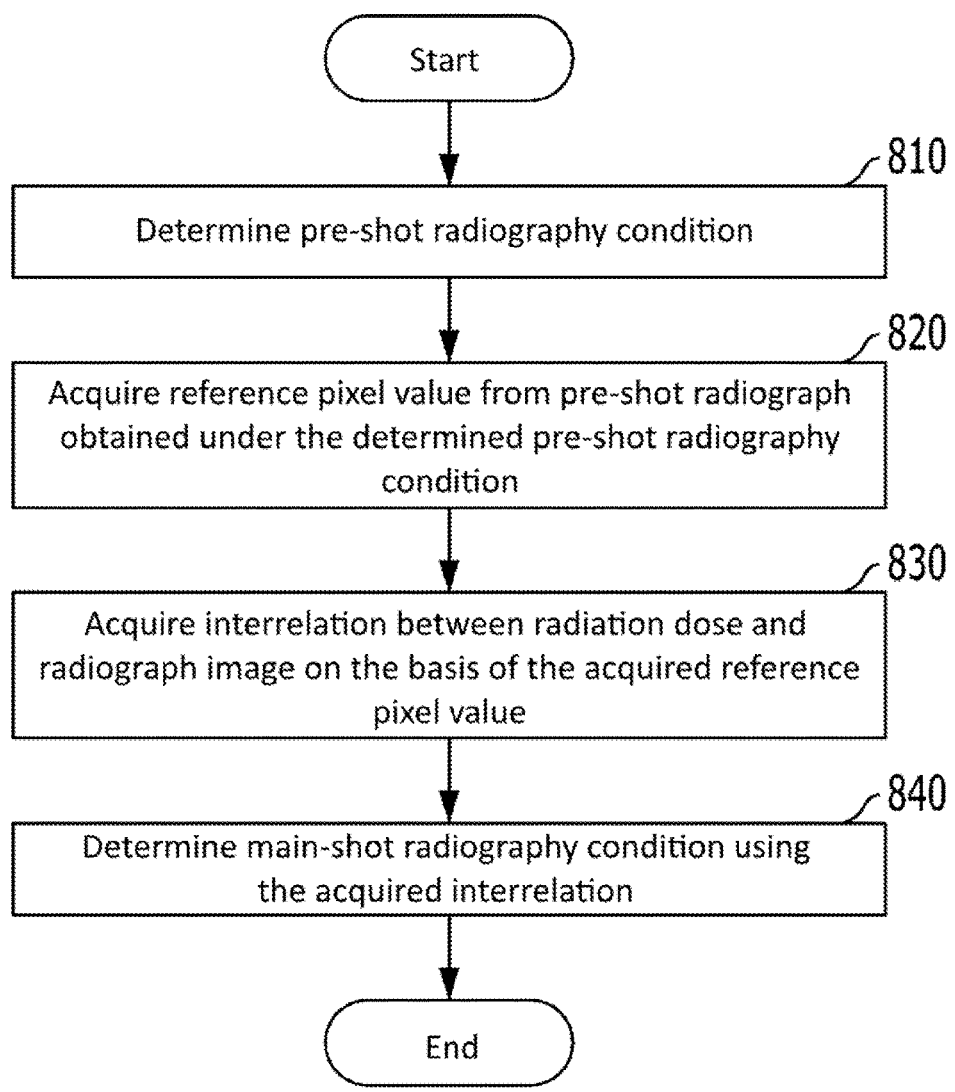
FIG. 11 is a diagram showing a method of adjusting an X-ray in a digital X-ray image system according to an embodiment of the present invention.

FIG. 11 is a flowchart illustrating an X-ray control method in a digital X-ray image system according to an embodiment of the present invention and a detailed embodiment of the method is the same as the above description, so the operational process is described.

First, the pre-shot radiography condition determiner 210 determines a radiography condition (810).

The radiography condition includes a pre-shot tube voltage (kVp) and a pre-shot radiation dose (mAs), in which the pre-shot tube voltage can be calculated by substituting a pre-shot tube voltage according to an actual breast thickness obtained from Equation 2, that is, the actual breast thickness into the graph indicated by kVp in FIG. 10 and the pre-shot radiation dose (mAs) is the minimum radiation dose, for example, 5 mAs. Further, the pre-shot radiography condition determiner 210 may consider the kind of a filter, as shown in FIG. 3, when determining the pre-shot tube voltage.

Thereafter, the reference pixel value acquirer 220 acquires a reference pixel value from a pre-shot radiograph obtained in accordance with the determined pre-shot condition (820).

In this case, the reference pixel value is the pixel value in the area having the lowest signal in the pre-shot radiograph and can be acquired by comparing luminance at positions in a pre-shot radiography, as shown in FIG. 4, or scanning a pre-shot radiography, as shown in FIG. 5.

Thereafter, the interrelation acquirer 230 acquires the interrelation between a radiation dose (mAs) and a radiograph signal on the basis of the acquired reference pixel value (830).

The interrelation between the radiation dose and the radiograph is a linear relation such as y=ax+b, as shown in FIG. 7.

Thereafter, the main-shot radiography condition determiner 240 determines a main-shot radiography condition using the acquired interrelation (840).

The main-shot radiography condition determiner 240, in order to determine the main-shot radiation dose for the main-shot radiography condition, calculates a target pixel value (TPV) by substituting an actual breast thickness into Equation 3 or the graph indicated by Target in FIG. 10, and determines a main-shot radiation dose as a main-shot radiography condition for a target pixel value, as shown in FIG. 8, using the interrelation between a radiation dose (mAs) and a radiograph signal shown in FIG. 7. Further, it checks whether the calculated main-shot radiation dose is in an effective range between the maximum (mAsmax) and the minimum (mAsmin) of the radiation dose that can be inputted for each breast thickness shown in FIG. 9, and determines the final main-shot radiation dose by correcting the calculated main-shot radiation dose within the effective range, if necessary.

Further, the main-shot tube voltage is determined the same as the pre-shot tube voltage determined before by the pre-shot radiography condition determiner 210.

Thereafter, the mammography apparatus 100 finally performs main-shot radiography at the main-shot radiation dose and the main-shot tube voltage determined by the main-shot radiography condition determiner 240.

As a result, a main-shot radiograph obtained using the X-ray irradiation controlling device and a method thereof in the digital X-ray image system according to the present invention shows a luminance difference within a critical value (for example, within 10%) at the highest-density area (for example, an interesting area).

The X-ray irradiation controlling device and a method thereof in the digital X-ray image system according to the present invention can be achieved in the types of programming commands that can be executed by various computers, and can be recorded on computer-readable media. The computer-readable media may include program commands, data files, and data structures of combinations thereof. The program commands that are recorded on the media may be those specifically designed and configured for the present invention or may be those available and known those engaged in the art of computer software. The computer-readable recording media include magnetic media such as hard disk, floppy disk, and magnetic tape, optical media such as CD-ROM and DVD, magneto-optical media such as floptical disk, and hardware devices specifically configured to store and execute program commands, such as ROM, RAM, and flash memory. The medium may be a transmission medium such as a metal wire or a waveguide for transmitting light including a carrier for transmitting signals designating program instructions and data structures. The program commands include not only mechanical languages made by a compiler, but high-class language codes that can be executed by a computer using an interpreter. The hardware device may be configured to operate as one or more software modules to perform the operation of the present invention, and vice versa.

Although the present invention was described with reference to limited embodiments and drawings, the present invention is not limited to the embodiments and may be changed and modified in various ways by those skilled in the art without departing from the spirit of the present invention described in claims.

Therefore, the scope of the present invention should not be limited to the embodiment(s), but should be determined by not only the following claims, but equivalents of the claims.

The invention claimed is:

1. An X-ray irradiation controlling device comprising:
a pre-shot radiography condition determiner determining a radiography condition;
a reference pixel value acquirer acquiring a reference pixel value from a pre-shot radiograph obtained under the pre-shot radiography condition;

an interrelation acquirer acquiring interrelation between a radiography condition and a radiograph signal on the basis of the reference pixel value; and a main-shot radiography condition determiner determining a main-shot radiography condition using the interrelation, wherein the radiography condition is a radiation dose, and wherein the main-shot radiography condition determiner determines the main-shot radiography condition such that the reference pixel value shows a desired target pixel value in a main-shot radiograph obtained under the main-shot radiography condition.

2. The device of claim 1, wherein the pre-shot radiography condition includes a pre-shot tube voltage and a pre-shot radiation dose, and the pre-shot radiography condition determiner determines the pre-shot tube voltage in accordance with a thickness of an object and determines the pre-shot radiation dose to a predetermined radiation dose.

3. The device of claim 1, wherein the reference pixel value acquirer acquires a pixel value of an area having a lowest signal in the pre-shot radiograph as the reference pixel value.

4. The device of claim 1, wherein the main-shot radiography condition includes a main-shot tube voltage and a main-shot radiation dose, and the main-shot radiography condition determiner determines the main-shot tube voltage in accordance with a thickness of an object, determines the pixel value in accordance with the thickness of the object, and determines a main-shot radiation dose for the target pixel value from interrelation between the radiation dose and the radiograph image.

5. The device of claim 1, wherein the main-shot radiography condition determiner controls the main-shot radiography condition so that a luminance difference at highest-density areas of main-shot radiographs is within a critical value.

* * * * *